United States Patent

Watanabe et al.

[11] Patent Number: 4,599,440
[45] Date of Patent: Jul. 8, 1986

[54] ORGANOCYCLOSILOXANE

[75] Inventors: Junichiro Watanabe; Yuichi Funahashi, both of Ohta, Japan

[73] Assignee: Toshiba Silicone Co., Ltd., Japan

[21] Appl. No.: 771,372

[22] Filed: Aug. 30, 1985

[30] Foreign Application Priority Data

Sep. 26, 1984 [JP] Japan .................................. 59-201179

[51] Int. Cl.$^4$ .............................................. C07F 7/08
[52] U.S. Cl. ........................................ 556/460; 556/451
[58] Field of Search ................................ 556/451, 460

[56] References Cited

U.S. PATENT DOCUMENTS 4,365,085 12/1982 Bartels-Keith et al. ......... 556/460 X Primary Examiner—Paul F. Shaver
Attorney, Agent, or Firm—Gary L. Loser

[57] ABSTRACT

Disclosed is an organocyclosiloxane which comprises a compound having the following formula:

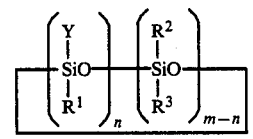

wherein $R^1$, $R^2$ and $R^3$, which may be the same or different, represent a hydrogen atom or a monovalent hydrocarbon group having 1 to 8 carbon atoms; Y represents

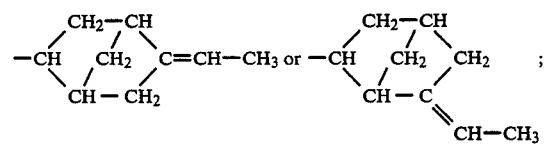

m is an integer of 3 to 5 and n is an integer of 1 to m.

3 Claims, 1 Drawing Figure

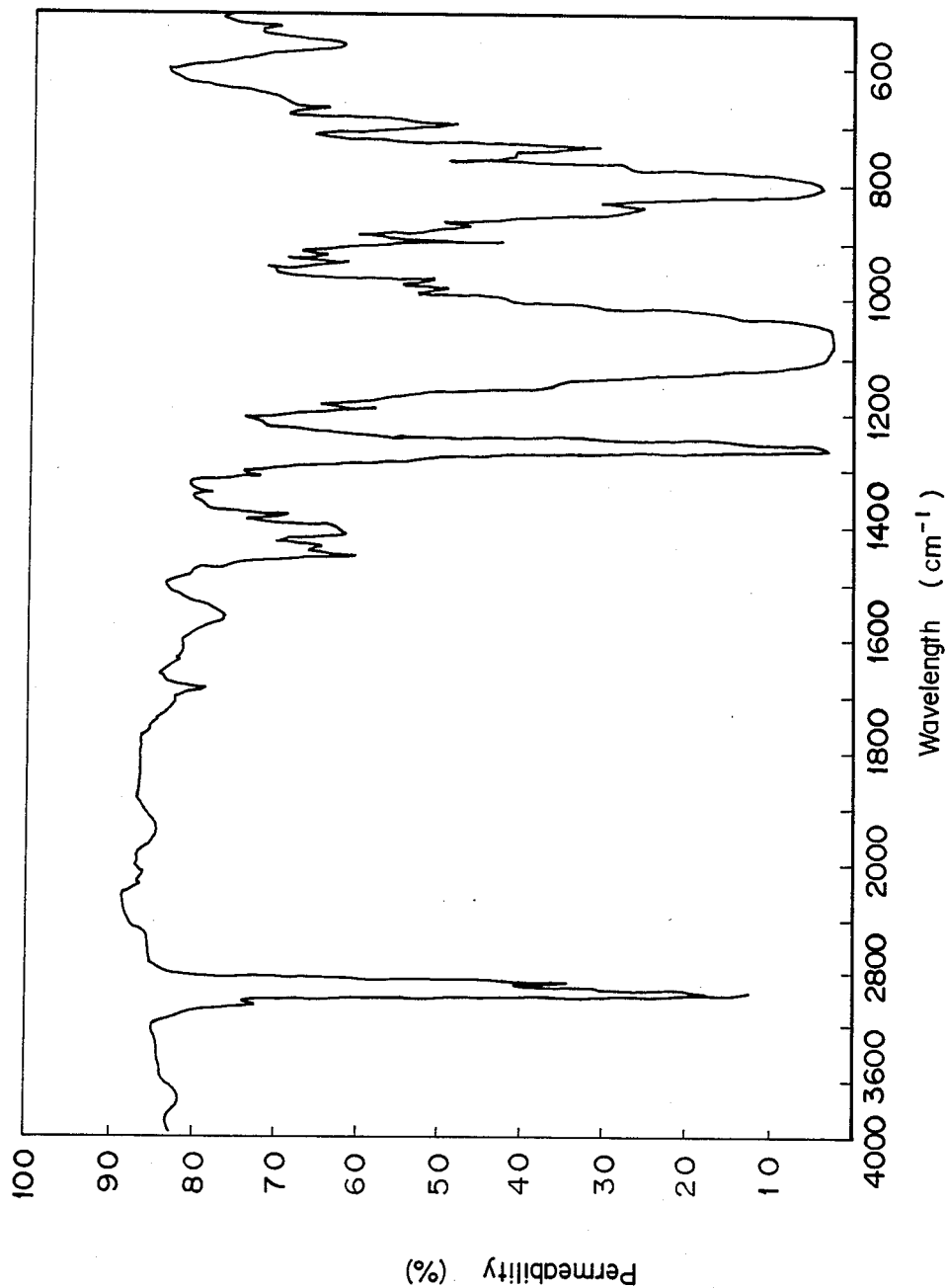

ORGANOCYCLOSILOXANE

The present application claims priority of Japanese patent application Ser. No. 84/201179 filed Sept. 26, 1984.

BACKGROUND OF THE INVENTION

The present invention relates to a novel and useful organocyclosiloxane having an ethylidene norbornyl group.

In general, in an addition type silicone elastomer which has widely been used, cross-linking thereof has been carried out through a vinyl group in most cases. Accordingly, a siloxane having a vinyl group is well known but a siloxane which has a condensed cyclic type hydrocarbyl group having an aliphatic unsaturated side chain has not yet been known.

SUMMARY OF THE INVENTION

The present inventors have carried out extensive studies concerning a siloxane which as a condensed cyclic type hydrocarbyl group having an aliphatic unsaturated side chain to accomplish the present invention.

That is, the organocyclosiloxane of the present invention comprises a compound having the following formula:

$$\left[ \begin{array}{c} Y \\ | \\ -SiO- \\ | \\ R^1 \end{array} \right]_n \left[ \begin{array}{c} R^2 \\ | \\ -SiO- \\ | \\ R^3 \end{array} \right]_{m-n}$$

wherein $R^1$, $R^2$ and $R^3$, which may be the same or different, represent a hydrogen atom or a monovalent hydrocarbon group having 1 to 8 carbon atoms; Y represents $$-CH\underset{CH-CH_2}{\overset{CH_2-CH}{\diagup}}\underset{}{\overset{}{\diagdown}}CH_2\;C=CH-CH_3 \text{ or } -CH\underset{CH-C}{\overset{CH_2-CH}{\diagup}}\underset{}{\overset{}{\diagdown}}CH_2\underset{CH-CH_3}{\overset{}{\diagdown}};$$

m is an integer of 3 to 5 and n is an integer of 1 to m.

BRIEF DESCRIPTION OF THE DRAWING

FIG. 1 illustrates an infrared absorption spectrum of the mixture obtained in Example 1.

DESCRIPTION OF THE INVENTION

In the above general formula, examples of the $R^1$, and $R^2$ and $R^3$ may include, in addition to a hydrogen atom, a methyl group, an ethyl group, a propyl group, a butyl group, a pentyl group, a hexyl group, a phenyl group and the like. Among these, the methyl group is preferred since it is easy to obtain a starting intermediate compound and ease of synthesis.

While m can be an integer of 3 to 5, it is preferred that m is 4 for ease of obtaining a starting intermediate compound and ease of synthesis.

Further, n is an integer of 1 to m, particularly preferred is an integer of 1 to 4.

In order to have at least one of characteristic groups of:

$$-CH\underset{CH-CH_2}{\overset{CH_2-CH}{\diagup}}\underset{}{\overset{}{\diagdown}}CH_2\;C=CH-CH_3 \text{ or } -CH\underset{CH-C}{\overset{CH_2-CH}{\diagup}}\underset{}{\overset{}{\diagdown}}CH_2\underset{CH-CH_3}{\overset{}{\diagdown}}$$

in the organocyclosiloxane of the present invention, n cannot be 0.

Exemplary compounds of the organocyclosiloxane of the present invention are illustrated below, wherein Y has the same meaning as defined above.

$$\left[ \begin{array}{c} Y \\ | \\ -SiO- \\ | \\ CH_3 \end{array} \right] \left[ \begin{array}{c} CH_3 \\ | \\ -SiO- \\ | \\ CH_3 \end{array} \right]_3,$$

$$\left[ \begin{array}{c} Y \\ | \\ -SiO- \\ | \\ CH_3 \end{array} \right]_2 \left[ \begin{array}{c} CH_3 \\ | \\ -SiO- \\ | \\ CH_3 \end{array} \right]_2,$$

$$\left[ \begin{array}{c} Y \\ | \\ -SiO- \\ | \\ CH_3 \end{array} \right]_3 \left[ \begin{array}{c} CH_3 \\ | \\ -SiO- \\ | \\ CH_3 \end{array} \right], \left[ \begin{array}{c} Y \\ | \\ -SiO- \\ | \\ CH_3 \end{array} \right]_4,$$

$$\left[ \begin{array}{c} Y \\ | \\ -SiO- \\ | \\ CH_3 \end{array} \right] \left[ \begin{array}{c} H \\ | \\ -SiO- \\ | \\ CH_3 \end{array} \right] \left[ \begin{array}{c} CH_3 \\ | \\ -SiO- \\ | \\ CH_3 \end{array} \right]_2,$$

$$\left[ \begin{array}{c} Y \\ | \\ -SiO- \\ | \\ C_2H_5 \end{array} \right] \left[ \begin{array}{c} C_2H_5 \\ | \\ -SiO- \\ | \\ C_2H_5 \end{array} \right]_3,$$

$$\left[ \begin{array}{c} Y \\ | \\ -SiO- \\ | \\ C_6H_5 \end{array} \right] \left[ \begin{array}{c} C_6H_5 \\ | \\ -SiO- \\ | \\ C_6H_5 \end{array} \right]_3, \left[ \begin{array}{c} Y \\ | \\ -SiO- \\ | \\ CH_3 \end{array} \right] \left[ \begin{array}{c} CH_3 \\ | \\ -SiO- \\ | \\ CH_3 \end{array} \right]_2,$$

$$\left[ \begin{array}{c} Y \\ | \\ -SiO- \\ | \\ CH_3 \end{array} \right] \left[ \begin{array}{c} CH_3 \\ | \\ -SiO- \\ | \\ CH_3 \end{array} \right]_4 \text{ and } \left[ \begin{array}{c} Y \\ | \\ -SiO- \\ | \\ CH_3 \end{array} \right]_2 \left[ \begin{array}{c} CH_3 \\ | \\ -SiO- \\ | \\ CH_3 \end{array} \right]_3.$$

These organocyclosiloxane can be synthesized by, for example, reacting an organohydrogencyclosiloxane represented by the formula:

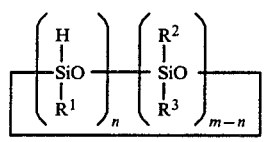

(I)

with 5-ethylidenebicyclo(2,2,1)hept-2-ene represented by the formula:

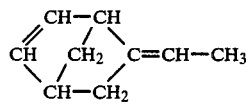

(II)

as starting materials.

The reaction can be carried out by using an equimolar or more, preferably, 1.0 to 2.0 moles of the 5-ethylidenebicyclo(2,2,1)hept-2-ene (II) based on the molar number of Si-H bonding of the organohydrogen cyclosiloxane (I), and carrying out the addition reaction in the presence of a platinum compound such as chloroplatinic acid, etc., as a catalyst to obtain the desired product. The conditions of the addition reaction depend on the final product to be obtained, but generally the reactants are heated at 30° to 180° C. for 5 to 50 hours. The final product can generally be obtained as a mixture of two compounds since two kinds of addition reactions to the compound (II) have been presented, and the product can be used as it is or after separation thereof by a known method for producing an elastomer and the like.

EXAMPLES

In the following, the present invention will be explained by referring to the Examples. In the Examples, all parts are by weight.

EXAMPLE 1

In a flask equipped with a dropping funnel were charged 180 parts of 5-ethylidenebicyclo(2,2,1)hept-2-ene and 0.04 part of chloroplatinic acid as a catalyst and the mixture was heated to 130° C. Then, 282 parts of heptamethylcyclotetrasiloxane was gradually added dropwise from the dropping funnel while keeping the temperature of the mixture at 130° C. and the addition reaction was carried out for 10 hours. Under reduced pressure (10 mmHg), stripping was carried out at 130° C. to remove the unreacted materials and then distillation was carried out to obtain 300 parts (Yield: 75%) of a mixture of the compounds (a) and (b) shown below in a ratio of 1.2:1.

Compound (a):

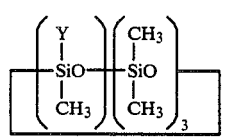

wherein

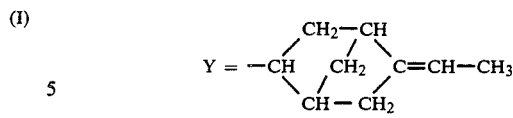

Compound (b):

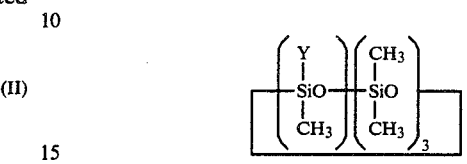

wherein

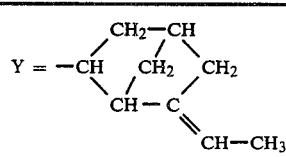

| | Boiling point: | 118° C./3.5 mmHg |
|---|---|---|
| | Refractive index ($n_D^{25}$): | 1.448 |
| | Specific gravity: | 0.999 |
| | Molecular weight: | 402 |
| | (by gas-mass spectrum analysis) | |
| | Elemental analysis: | |
| | Observed | Calculated (as $C_{16}H_{34}O_4Si_4$) |
| C | 48.1 | 47.8 |
| H | 8.5 | 8.4 |
| O | 15.6 | 15.9 |
| Si | 27.8 | 27.9 |

Infrared absorption spectrum: shown in FIG. 1.

EXAMPLE 2

In a flask equipped with a dropping funnel were charged 300 parts of 5-ethylidenebicyclo(2,2,1)hept-2-ene and 0.06 part of chloroplatinic acid as a catalyst and the mixture was heated to 130° C. Then, 268 parts of hexamethylcyclotetrasiloxane was gradually added dropwise from the dropping funnel while keeping the temperature of the mixture at 130° C. and the addition reaction was carried out for 15 hours. Under reduced pressure (10 mmHg), stripping was carried out at 130° C. to remove the unreacted materials and then distillation was carried out to obtain 355 parts (Yield: 70%) of a mixture of the compounds (c) and (d) shown below in a ratio of 1:1.

Compound (c):

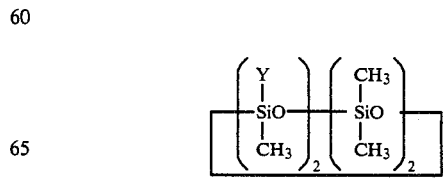

wherein $$Y = -CH \begin{array}{c} CH_2-CH \\ CH_2 \\ CH-CH_2 \end{array} C=CH-CH_3$$

Compound (d):

$$\left[\begin{array}{c} Y \\ | \\ SiO \\ | \\ CH_3 \end{array}\right]_2 \left[\begin{array}{c} CH_3 \\ | \\ SiO \\ | \\ CH_3 \end{array}\right]_2$$

wherein $$Y = -CH \begin{array}{c} CH_2-CH \\ CH_2 \\ CH-C \end{array} CH_2 \atop CH-CH_3$$

| Boiling point: | 180 to 190° C./4 mmHg |
| --- | --- |
| Refractive index ($n_D^{25}$): | 1.474 |
| Specific gravity: | 1.026 |
| Molecular weight: | 508 |
| | (by gas-mass spectrum analysis) |

| Elemental analysis: | | |
| --- | --- | --- |
| | Observed | Calculated (as $C_{24}H_{44}O_4Si_4$) |
| C | 57.0 | 56.7 |
| H | 8.8 | 8.7 |
| O | 12.4 | 12.6 |
| Si | 21.8 | 22.0 |

EXAMPLE 3

The same procedures as in Example 1 were carried out except that heptamethylcyclotetrasiloxane in Example 1 was replaced with 208 parts of pentamethylcyclotrisiloxane to obtain 226 parts (Yield: 69%) of a mixture of the compounds (e) and (f) shown below in a ratio of 1.1:1.

Compound (e):

$$\left[\begin{array}{c} Y \\ | \\ SiO \\ | \\ CH_3 \end{array}\right] \left[\begin{array}{c} CH_3 \\ | \\ SiO \\ | \\ CH_3 \end{array}\right]_2$$

wherein $$Y = -CH \begin{array}{c} CH_2-CH \\ CH_2 \\ CH-CH_2 \end{array} C=CH-CH_3$$

Compound (f):

$$\left[\begin{array}{c} Y \\ | \\ SiO \\ | \\ CH_3 \end{array}\right]_2 \left[\begin{array}{c} CH_3 \\ | \\ SiO \\ | \\ CH_3 \end{array}\right]_2$$

wherein $$Y = -CH \begin{array}{c} CH_2-CH \\ CH_2 \\ CH-C \end{array} CH_2 \atop CH-CH_3$$

| Boiling point: | 95 to 105° C./5 mmHg |
| --- | --- |
| Molecular weight: | 328 |
| | (by gas-mass spectrum analysis) |

| Elemental analysis: | | |
| --- | --- | --- |
| | Observed | Calculated (as $C_{14}H_{28}O_3Si_3$) |
| C | 51.0 | 51.2 |
| H | 8.5 | 8.6 |
| O | 14.9 | 12.6 |
| Si | 25.6 | 25.6 |

EXAMPLE 4

The same procedures as in Example 1 were carried out except that heptamethylcyclotetrasiloxane in Example 1 was replaced with 356 parts of nonamethylcyclopentasiloxane to obtain 309 parts (Yield: 65%) of a mixture of the compounds (g) and (h) shown below in a ratio of 1.1:1.

Compound (g):

$$\left[\begin{array}{c} Y \\ | \\ SiO \\ | \\ CH_3 \end{array}\right] \left[\begin{array}{c} CH_3 \\ | \\ SiO \\ | \\ CH_3 \end{array}\right]_4$$

wherein $$Y = -CH \begin{array}{c} CH_2-CH \\ CH_2 \\ CH-CH_2 \end{array} C=CH-CH_3$$

Compound (h):

$$\left[\begin{array}{c} Y \\ | \\ SiO \\ | \\ CH_3 \end{array}\right] \left[\begin{array}{c} CH_3 \\ | \\ SiO \\ | \\ CH_3 \end{array}\right]_4$$

wherein

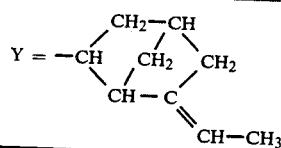

| Boiling point: | 160 to 180° C./5 mmHg |
| --- | --- |
| Molecular weight: | 476 |
| | (by gas-mass spectrum analysis) |

Elemental analysis:

| | Observed | Calculated (as $C_{18}H_{40}O_5Si_5$) |
| --- | --- | --- |
| C | 45.8 | 45.4 |
| H | 8.5 | 8.4 |
| O | 16.5 | 16.8 |
| Si | 29.2 | 29.4 |

The compound of the present invention can be used, by utilizing the double bond being contained therein, as a cross-linking agent of polydiorganosiloxane which has been used as a main starting material of a silicone elastomer, and thus can be widely applied to the production of an elastomer.

We claim:

1. An organocyclosiloxane comprising a compound having the following formula:

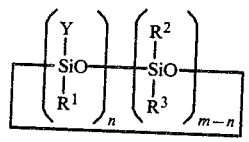

wherein $R^1$, $R^2$ and $R^3$, which may be the same or different, represent a hydrogen atom or a monovalent hydrocarbon group having 1 to 8 carbon atoms; Y represents

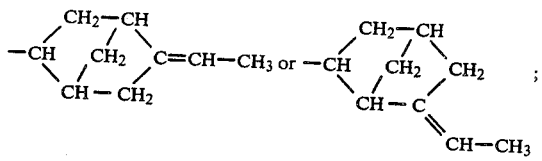

m is an integer 3 to 5 and n is an integer of 1 to m.

2. An organocyclosiloxane according to claim 1, wherein said m is 4.

3. An organocyclosiloxane according to claim 1, wherein said $R^1$, $R^2$ and $R^3$ are methyl groups.

* * * * *